United States Patent [19]

Ivie et al.

[11] Patent Number: 4,665,388

[45] Date of Patent: May 12, 1987

[54] SIGNALLING DEVICE FOR WEIGHT LIFTERS

[76] Inventors: Bernard Ivie, Rt. 1, 19 Alesia Dr., East Prairie, Mo. 63845; Michael R. Miller, 302 Charles La., Sikeston, Mo. 63801

[21] Appl. No.: 668,625

[22] Filed: Nov. 5, 1984

[51] Int. Cl.$^4$ .................. G08B 21/00; A63B 69/00
[52] U.S. Cl. .................................. 340/573; 272/119; 272/123; 272/DIG. 5; 200/DIG. 2
[58] Field of Search ................ 272/DIG. 5, 119, 116, 272/143, 123; 273/54 B; 200/DIG. 2; 340/573, 574, 575, 576, 686, 687, 688, 689, 691; 362/802

[56] References Cited

U.S. PATENT DOCUMENTS 3,614,763 10/1971 Yannuzzi ...................... 340/573 X
3,634,885 1/1972 Barkley ........................ 340/573
3,644,919 2/1972 Mathauser .................... 340/573

Primary Examiner—Robert A. Hafer
Assistant Examiner—Arnold W. Kramer
Attorney, Agent, or Firm—Cox & Smith Inc.

[57] ABSTRACT

A signalling device for weight lifters performing exercises involving bending of the knees. The signalling device is provided with mercury switch for sensing deviation of the axis of the portion of the leg to which the device is attached and a buzzer or other signalling device which signals the lifter when that portion of the leg has deviated from the vertical by a preselected amount. The amount of deviation from the vertical required to activate the signalling device may be varied by an optional angle adjustment. The signalling device allows a weight lifter to exercise properly, but effectively, without risking injury.

8 Claims, 5 Drawing Figures

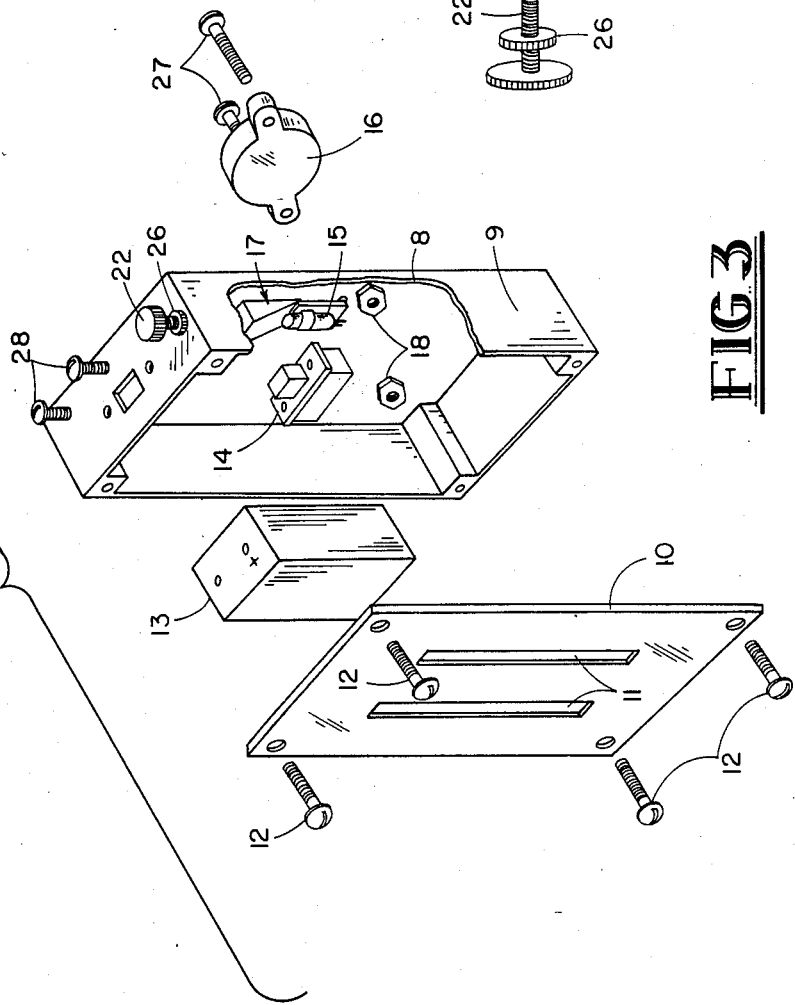
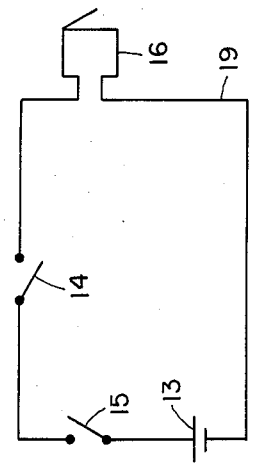
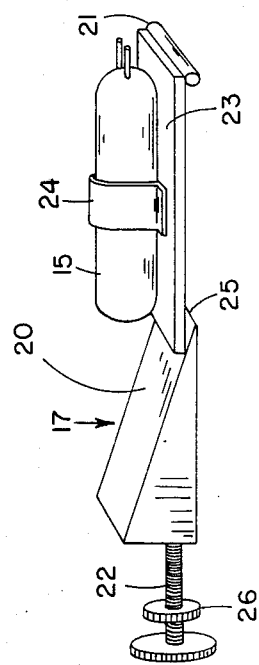
FIG. 3
FIG. 4
FIG. 5

SIGNALLING DEVICE FOR WEIGHT LIFTERS

BACKGROUND OF THE INVENTION

The present invention pertains to a device and method of correctly performing exercises. More particularly it pertains to a device which signals a weight lifter who is in the process of performing a lift when the lifter's thighs are rotated to a specific angle.

Athletes who lift weights often perform a lift called the "parallel squat" lift. The "full" parallel squat is a lift in which an athlete begins in a standing position, with a barbell or other weight resting on his shoulders, behind his neck. The lifter must have both hands on the bar of the barbell, chest out, lower back pulled in, head up, and both feet flat on the floor. To begin the lift, the athlete begins to lower his hips, by bending at the knees, keeping the chest, back, head and feet in the original position while forcing the knees outward. The athlete continues lowering the hips until the upper thighs drop slightly below a line parallel to the surface upon which the athlete is standing. Then the process is reversed until the athlete is standing in a full upright position again. To perform the "half" squat, the lifter begins the lift in the same manner, but reverses before the thighs are parallel to the ground.

The part of the full squat which is the most difficult to perform properly is reaching and stopping the lift when the upper thighs reach that point at which they are slightly below a line horizontal to the knees. Because the athlete must keep his head up, he cannot see a profile of himself performing the lift or look down at the position of his upper thighs. A person performing the lift by himself will only known when the proper point has been reached in the lift by "feel" or experience. Watching a mirror image is often unsatisfactory for athletes because of the distraction, the danger of having glass around heavy weights, and the high cost of full length mirrors. The difficulty is in identifying that point at which the lifter should stop and start back up to finish the exercise. If the upper thighs are not lowered far enough, the correct muscles are not utilized and the benefits of the lift are not realized.

If the thighs go too low, there is a serious danger of injury. When the athlete reaches the low point of the lift and starts to reverse direction, there is a tendency to "bounce" at the bottom of the lift. This bouncing can cause sudden stress to the knee or thigh muscles, resulting in injuries such as weakening of the knee or pulling the muscles in the thigh.

To a somewhat lesser extent, the same type of problems exist when the athlete performs the half squat.

The parallel squat lift is performed by any number of weight lifters as a form of exercise, but is also performed in weight lifting competitions. When other persons are present to watch the lift, such as judges in weight lifting competitions, the previous method of determing the proper point at which the lift should be reversed is still inadequate. The judgment of the person watching the lift is subject to the fallacies of the human eye. Also, there is a delay between when the person watching the lift sees that the proper point has been reached, and when he is able to communicate that information to the lifter by some type of warning. Thus, there is a danger this delay will allow the lifter to go too low. Corresponding problems are found in other types of lifts involving other members of the body.

Reference is made to U.S. Pats. Nos. 3,766,538 issued to Dealy; 3,644,919 issued to Mathauser; and 1,956,201 issued to Roberts. The Mathuaser and Roberts patents are specifically limited to skiers and boxers, respectively. The Dealy patent is apparently intended for use primarily by baseball players and it involves a different concept than that embodied in the present invention because it seeks to detect motion in a particular area of the body so that the timing of the person's movement can be sensed. In other words, the Dealy device is intended to let the user know if a particular part of his body has been moved and when it was moved. It is apparently not intended to tell the athlete if the particular part of the body moves properly to a certain point and stops. Thus, it is an object of the present invention to provide a monitoring device for weight lifters which signals the lifter when the particular body part monitored has moved far enough to complete a lift.

It is another object of the present invention to allow weight lifters to determine whether they have correctly completed the lift when by themselves.

Another object of the present invention is to provide a reliable and immediate response to those observing the lift when the lift has been correctly completed.

Another object of the invention is to allow weight lifters performing a parallel squat lift to go low enough to successfully complete the lift without going so low as to risk injury.

Also, it is an object of the present invention to provide a device which will work on any athlete and is easily interchangable.

Finally, it is an object of the present invention to provide weight lifters with a means of telling whether the chest, back, and feet have been kept in the correct positions during a parallel squat lift.

SUMMARY OF THE INVENTION

These objects are achieved in the present invention by providing a signalling device for use by an athlete during an exercise involving the bending of the athlete's knees which includes a signalling means, means for attaching the signalling means to a portion of the leg of an athlete, and means for sensing a preselected amount of deviation of the axis of that portion of the athlete's leg from the vertical. The deviation sensing means operates to electrically actuate the signalling means when the preselected amount of deviation is reached by the bending of the knees of the athlete.

BRIEF DESCRIPTION OF DRAWING

FIG. 3 is an exploded perspective view of the bottom of the signalling device of the present invention with a portion of the cover of the device being cut away to show the various components.

FIG. 4 is a side perspective view of the optional manual screw adjustment of the mercury switch.

FIG. 5 is a diagram of the circuit of the signalling device of the present invention.

DESCRIPTION OF THE PREFERRED EMBODIMENT

Figure 1:
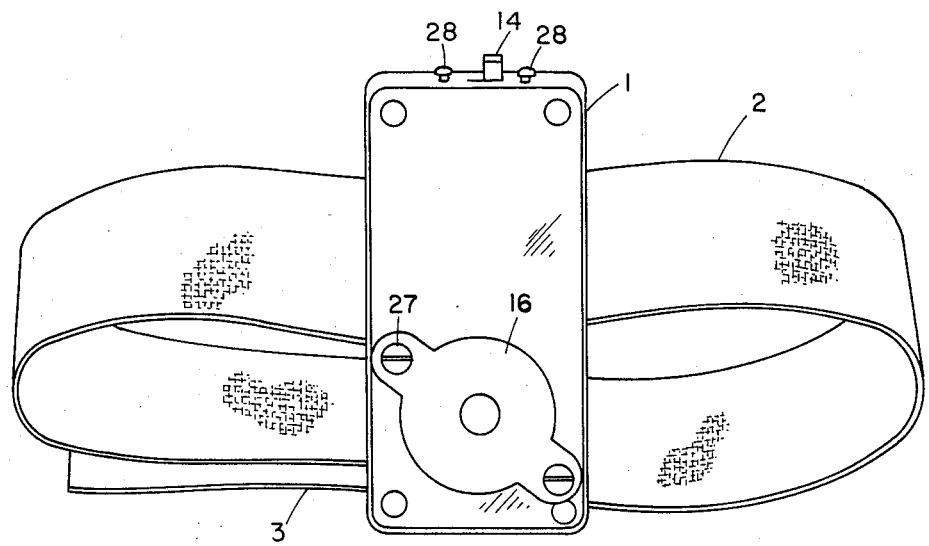
FIG. 1 is a front perspective view showing the signalling device of the present invention.

Referring to FIG. 1, there is shown a signalling device 1 which is mounted on a belt 2. The belt 2 may be of any width, thickness, or length so that it can support the signalling device 1 but still remain flexible and comfortable enough to be used by lifters around any part of the body. The belt 2 may be made of any material well known in the art, so that it remains flexible and comfortable, and is preferably capable of stretching. The fastening means 3 of the belt 2 is a fastening means such as that sold under the trademark VELCRO, or buckles or other fastening means which are known in the art. The belt 2 is wrapped around the portion of the body critical to the particular lift being done. The belt 2 is then closed by the fastening means 3, and the signalling device 1 is switched on by the on-off switch 14. The lift is then started, and the signalling means 16 signals the lifter when the proper position of the lift is achieved.

Figure 2:
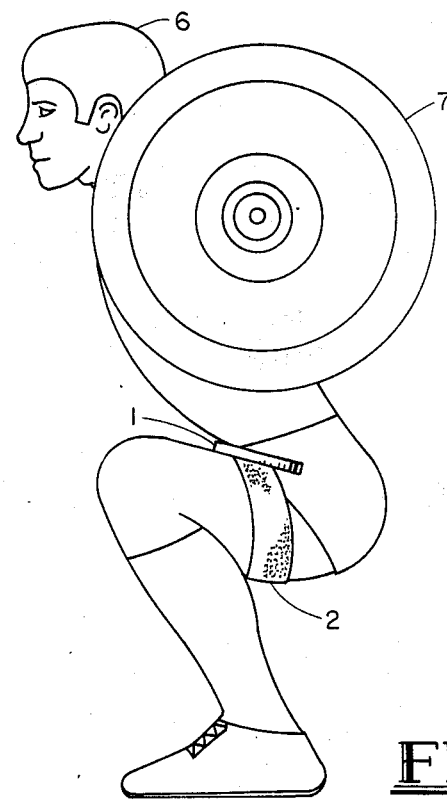
FIG. 2 is a side view of a preferred embodiment of the invention, showing the device attached to the upper thigh of a weight lifter performing a parallel squat lift.

FIG. 2 shows a preferred embodiment of the present invention as it would be worn by a weight lifter 6 performing a parallel squat lift. The lifter 6 is holding a set of barbell weights 7 with the bar resting on the back of the lifter's neck and on top of the shoulders. The lifter 6 has the signalling device 1 strapped to the mid-thigh by the belt 2. The axis of the lifter's thighs are just just past the horizontal; this particular position of the lifter 6 being the correct position for the lowest point of the parallel squat lift. This is the point where the lifter 6 should reverse his downward motion and start back up.

Referring to FIG. 3, the signalling device 1 is contained in a box formed by a cover 9 and back plate 10. The two pieces are constructed of plastic or any other material known in the art. The back plate 10 has two rectangular slots 11 cut out of it so that the belt 2 may be passed through them to attach the signalling device 1 to the belt 2. The back plate 10 is attached to the cover 9 by screws, or any other attachment means known in the art that would allow the signalling device 1 to be easily opened. FIG. 3 shows a preferred embodiment of four screws 12 to attach the back plate 10 to the cover 9.

The interior of the signalling device 1 contains a power source 13, a manual on-off switch 14, a mercury switch 15, and a signalling means 16. An optional angle adjustment means 17 for the mercury switch 15 is also shown in place within the cover 9 in FIG. 3 and in enlarged perspective in FIG. 4. The power source 13, on-off switch 14, mercury switch 15, signalling means 16, and angle adjustment means, indicated generally at 17, is attached to the interior of the hollow rectangular box 9 by screws, or by clips, glue, pins, or any other attaching means known in the art. In the preferred embodiment of the invention shown in FIG. 3, the signalling means 16 is attached to the cover 9 by screws 27 and nuts 18 and the on-off switch 14 is attached by screws 28.

Power source 13 is a small battery or other type of power source known in the art. The on-off switch 14 is also known in the art. The signalling means 16 is any buzzer, beeper or other electric signalling means known in the art, as long as the signalling means emits a signal loud enough to be suitable in a weight lifting environment. Visual signalling means are also contemplated. It is understood that the power source 13, on-off switch 14, mercury switch 15, and signalling means 16 shown in FIG. 3 are connected by wires 19 in accordance with the simple circuit shown in FIG. 5. For purposes of clarity, the wires have been omitted from FIGS. 3 and 4.

In an alternative embodiment of the present invention (not shown), a rheostat is provided in the circuit between switch 14 and signalling means 16 to allow the athlete to control the volume of the signal emitted by signalling means 16. The control for the rheostat would protrude from cover 9 at a point which facilitates ease of adjustment by the athlete.

The optional angle adjustment mechanism shown in FIG. 4 is comprised of wedge 20, the point 25 of which will slide under a platform 23 upon which the mercury switch 15 is secured by clamp 24. The platform 23 is mounted with a hinge at one end 21 so that the wedge 20 can be used to adjust the angle at which the axis of the mercury switch 15 deviates from the vertical when the signalling device 1 is attached to the athlete's leg and the athlete is standing in the erect position. The wedge 20 is moved back and forth under the platform 23 by a screw or other means known in the art. The preferred embodiment shown in FIG. 4 includes a thumbscrew 22 to move the wedge 20 up and down along the inside wall of the cover 9. The thumbscrew 22 is manually operated and includes a stop 26 to stop the travel of the thumbscrew through the cover 9 when the stop 26 abuts the cover 9.

To use the device of the present invention, signalling device 1 is attached to a portion of the athlete's leg, particularly the thigh, by means of belt 2 and fastener 3. The on-off switch 14 is turned to the "on" position and the athlete then picks up the barbells and assumes an erect position. As the athlete begins the motion involved in performing the parallel squat lift by bending at the knees, the axis of the thigh of the athlete's leg begins to rotate through an arc. As soon as the axis of the thigh has rotated past 90 degrees from the vertical, the mercury switch 15 closes, completing the circuit and activating signalling means 16.

To use the device to signal the proper amount of rotation from the vertical in the performance of a half parallel squat, the thumbscrew 22 is rotated to cause the wedge 20 to move under the platform 23 and rotate the mercury switch 15 through a portion of the arc from the vertical even before the athlete begins the crouching motion. Consequently, when the sum of the degrees of rotation of the axis of the portion of the athlete's leg to which the device is attached caused by the bending at the knees and the degree of deviation of the axis of the switch from the vertical effected by the adjustment mechanism 17 exceeds 90 degrees from the vertical, the mercury switch 15 will close and the signalling means 16 is activated.

The present invention has been described according to the preferred embodiment shown. The present invention may be embodied in a number of structures which may differ from this preferred embodiment without departing from the spirit or scope of the present invention, which is limited only by the scope of the following claims.

What is claimed is:

1. A signalling device for use by an athlete during an exercise involving the bending of the athlete's knee comprising:
   container means;
   means for attaching said container means to a portion of the leg of an athlete;
   a mercury switch pivotally mounted at one end to said container means, the axis of said mercury switch being substantially vertical when said container means is attached to the portion of the athlete's leg and the axis of said pivot being substantially perpendicular to the axis of said mercury switch; and means mounted to said container means for moving a wedge up and down under said mercury switch to initially selectably pivot said mercury switch from said substantially vertical position so as to activate electrical signalling means when the portion of the athlete's leg reaches a preselected amount of deviation from the vertical by bending at the knee of the athlete so as to activate said mercury switch.

2. The signalling device of claim 11 additionally comprising a power source for powering said electrical signalling means when said electrical signalling means is activated by said mercury switch.

3. The signalling device of claim 2 additionally comprising means for switching said power source on and off.

4. The signalling device of claim 1 wherein said signalling means comprises means emitting an audible signal when activated by said mercury switch.

5. The signalling device of claim 1 wherein said attaching means comprises means for releasably fastening said container means around the portion of the athlete's leg.

6. A method of identifying that point at which a weight lifter should reverse directions while performing an exercise involving the lowering of a weight by bending at the knees in a squatting motion comprising:

attaching a container having a mercury switch pivotably mounted thereto to a portion of the leg of a weight lifter, the axis of the mercury switch being initially substantially vertical, the mercury switch being operable to activate a signalling means to signal that point at which the axis of the mercury switch deviates by more than ninety degrees from the initial substantially vertical position;

moving a wedge up or down to cause the axis of the mercury switch to pivot in a selected deviation from the initial substantially vertical position;

lowering a weight by bending at the knee of the weight lifter in a squatting motion;

stopping the lowering of the weight when the selected deviation from the initial substantially vertical position and the rotation of the axis of the portion of the leg of the athlete to which the container is attached exceeds ninety degrees from the vertical; and reversing the squatting motion and raising the weight by straightening the knee of the weight lifter.

7. The method of claim 6 wherein the axis of said portion of said weight lifter's leg deviates by more than 90 degrees from the vertical.

8. The method of claim 6 wherein said signalling means is adjusted to signal said deviation of more than 90 degrees from the vertical before said portion of said weight lifter's leg deviates from the vertical by more than 90 degrees.

* * * * *